United States Patent [19]

Hirano et al.

[11] Patent Number: 5,472,697
[45] Date of Patent: Dec. 5, 1995

[54] COMPOSITION FOR TREATING KERATINOUS FIBERS

[75] Inventors: Yuji Hirano, Chiba; Naohisa Kure, Tokyo, both of Japan

[73] Assignee: Kao Corporation, Tokyo, Japan

[21] Appl. No.: 182,122

[22] PCT Filed: Jun. 25, 1993

[86] PCT No.: PCT/JP93/00868

§ 371 Date: Feb. 3, 1994

§ 102(e) Date: Feb. 3, 1994

[87] PCT Pub. No.: WO94/00094

PCT Pub. Date: Jan. 6, 1994

[30] Foreign Application Priority Data

Jun. 29, 1992 [JP] Japan .................... 4-170911

[51] Int. Cl.⁶ .............. A61K 7/06; A61K 7/00
[52] U.S. Cl. ............ 424/401; 424/70.1; 424/70.2; 424/70.4; 424/401; 132/202
[58] Field of Search ............ 424/70–72, 70.1, 424/401, 70.2, 70.4; 132/202

[56] References Cited

U.S. PATENT DOCUMENTS

| | | | |
|---|---|---|---|
| 4,259,204 | 3/1981 | Homma | 252/174.16 |
| 4,300,900 | 11/1981 | Putzar | 8/524 |
| 4,306,873 | 12/1991 | Lapidus | 8/405 |
| 4,614,200 | 9/1986 | Hsiung | 132/7 |
| 4,828,750 | 5/1989 | Simion | 525/142 |
| 4,834,971 | 5/1989 | Klenk | 424/70 |
| 4,898,725 | 2/1990 | Hoeffkes | 424/70 |
| 5,009,813 | 4/1991 | Watanabe | 252/545 |
| 5,045,308 | 9/1991 | Spiegel | 424/61 |
| 5,254,336 | 10/1993 | Hoshowski | 424/70 |

Primary Examiner—Thurman K. Page
Assistant Examiner—Sally Gardner
Attorney, Agent, or Firm—Oblon, Spivak, McClelland, Maier, & Neustadt

[57] ABSTRACT

A composition for treating keratinous fibers, which comprises:
(A) A first agent containing a metal ion,
(B) A second agent comprising:
(B-1) An organic or inorganic compound which is capable of readily permeating into the keratinous fibers and can form water-insoluble or sparingly soluble complex together with said metal ion of component (A), and
(B-2) An organic compound which cannot readily permeate into the keratinous fibers, and which reacts with said metal ion of component (A) to form a water-soluble complex, and method for treating keratinous fibers utilizing the composition.

When the composition according to the present invention is used for treating keratinous fibers, it allows water-insoluble or sparingy soluble complex products to deposit inside the keratinous fibers while preventing water-insoluble or sparingly soluble complex products from depositing on the surface of the keratinous fibers. Because of this mechanism, the present composition is capable of imparting sufficient firmness and elasticity to keratinous fibers without inducing any objectionable rough or frictional feel to the touch of the hair.

13 Claims, No Drawings

COMPOSITION FOR TREATING KERATINOUS FIBERS

TECHNICAL FIELD

The present invention relates to a composition for treating keratinous fibers, and more particularly, to a composition for treating keratinous fibers which is capable of imparting favorable firmness and elasticity to keratinous fibers such as hair without giving rough feeling to the texture of the fibers, and also to a treatment method using the composition.

BACKGROUND ART

Several methods have conventionally been proposed to improve the firmness and elasticity of keratinous fibers such as hair, wool and other keratinous fibers for knitting or weaving. The following 1) to 4) may be mentioned as examples of such methods:

1) Polymers incorporated into a perming liquid or a hair dye composition are adsorbed onto the surface of the keratinous fiber (Japanese patent publication "Kokai" Nos. 52-7449 and 58-216113),
2) Protein hydrolysates are permeated into the keratinous fiber,
3) The keratinous fiber is shrinked by a shrinking agent (Japanese patent publication "Kokai" Nos. 55-108812, 58-109405 and 60-87208), and
4) A water-soluble substance is contacted with a keratinous fiber to form a water-insoluble or sparingly soluble salt inside the fiber (Japanese patent publication "Kokai" No. 1-233208).

However, these methods are not necessarily successful. In method 1) above, when the keratinous fibers are shampooed, the firmness and elasticity imparted to the fibers will easily be lost, because the polymers which had been adsorbed onto the surface of the fibers are washed away. In method 2) above, sufficient effect cannot be obtained because the protein hydrolysates to be used generally have molecular weights over several thousands, and this means that only a slight amount of protein hydrolysates can be permeated into the keratinous fiber. In method 3), metal ions are generally used as a shrinking agent. The shrinking effect is obtained from a chelating reaction between the metal ion and a functional group (mainly a carboxyl group) in the keratinous fiber. Therefore, when the keratinous fiber is shampooed with an ordinary shampoo which contains a chelating agent such as sodium ethylenediaminetetraacetate, a chelate exchanging reaction takes place, which causes a gradual extinguishment of the shrinking effect. Method 4) is good in that a certain degree of firmness and elasticity can be imparted, and they can last after the fibers undergo several shampooing. However, when the concentration of the active ingredients is raised with an aim to improve the effect, considerable amounts of water-insoluble or sparingly soluble salts deposit on the surface of the hair fiber, causing objectionable frictional and rough feeling of the hair.

Accordingly, compositions for treating keratinous fibers which can provide the fibers with excellent firmness and elasticity while avoiding objectionable frictional or rough feeling to the touch have still been desired.

DISCLOSURE OF INVENTION

Accordingly, the present invention provides a composition for treating keratinous fibers, which comprises:

(A) A first agent containing a metal ion, (B) A second agent comprising:
(B-1) An organic or inorganic compound which is capable of readily permeating into the keratinous fibers and can form a water-insoluble or sparingly soluble complex together with said metal ion of component (A), and
(B-2) An organic compound which cannot readily permeate into the keratinous fibers, and which reacts with said metal ion of component (A) to form a water-soluble complex.

The present invention also provides a method of treating keratinous fibers, where the fibers are treated with the above-mentioned first agent, and after a certain period of time, they are treated with the above-mentioned second agent.

BEST MODE FOR CARRYING OUT THE INVENTION

Examples of the metal ions which are components of the first agent (A) of the present composition include $Mg^{2+}$, $Ca^{2+}$, $Zn^{2+}$, $Ag^+$, $Al^{3+}$, $Ba^{2+}$, $Mn^{2+}$, $Fe^{2+}$, $Fe^{3+}$, $Ni^{2+}$, and the like. These ions are used in a form of a water-soluble salt such as chlorides, hydroxides, nitrates, sulfates, phosphates, acetates and carbonates.

These metal ions are used singly or in combination of two or more. It is preferred that the metal ions be incorporated into the first agent in amounts of from 0.05 to 20.0% by weight (hereinafter simply referred to as %), and especially 0.1 to 10.0% based on the total weight of the first agent. Amounts less than the above range will cause insufficient effects in providing the firmness, elasticity and volume of the keratinous fibers and also cause reduced lasting ability. On the other hand, amounts exceeding the above range will bring about excessive amounts of metal ion deposit on the surface of the keratinous fibers, which provides rough and frictional feeling to the touch of the fibers.

The function of the component (B-1) of the second agent is to provide the keratinous fibers with excellent firmness and elasticity for a prolonged period of time by forming water-insoluble or sparingly soluble complex as a result of the reaction between the permeated component (B-1) in the keratinous fibers and the above-mentioned metal ion (A). In view of this, it is necessary that the component (B-1) be readily permeable into the keratinous fiber and it is preferred that the molecular weight be 180 or less. The complex formed by the reaction between component (B-1) and metal ion (A) is insoluble in water or sparingly soluble in water. In detail, it is preferred that the complex have a Ksp value of $1.0 \times 10^{-5}$ or less at 25° C., or have a solubility of 0.2 g/100 g or less at 25° C.

Examples of inorganic sources of component (B-1) include chloride ion, hydroxide ion, nitride ion, sulfate ion, phosphate ion, borate ion, and carbonate ion. Examples of organic sources of component (B-1) include monocarboxylic acids and dicarboxylic acids. Among them, especially preferred are formic acid, acetic acid, propionic acid, butyric acid, isobutyric acid, valeric acid, isovaleric acid, sorbic acid, lactic acid, oxalic acid, malonic acid, succinic acid, glutaric acid, maleic acid, fumaric acid, citraconic acid, iraconic acid and tartaric acid. They are used in a form of a water-soluble salt such as sodium salts, potassium salts, ammonium salts and the like.

These components (B-1) are used singly or in combination of two or more. It is preferred that the component (B-1) be incorporated into the second agent in an amount of 0.1% or more, more preferably from 0.1 to 10.0%, and most preferably from 0.5 to 10.0% based on the total weight of the second agent. Amounts less than the above range will cause insufficient formation of water-insoluble or sparingly soluble complex in the hair fiber, which indicates that the firmness, elasticity and volume of the hair might be easily lost by everyday shampooing.

Examples of preferable combination of components (A) and (B-1) include calcium ion and oxalic acid (Ksp=$2.1 \times 10^{-9}$ at 25° C.), calcium ion and carbonic ion (Ksp=$4.7 \times 10^{-9}$ at 25° C.), calcium ion and phosphoric ion (Ksp=$2.0 \times 10^{-29}$ at 25° C.), calcium ion and sulfuric ion (Ksp=$2.4 \times 10^{-9}$ at 25° C.), magnesium ion and phosphoric ion (Ksp=$6.3 \times 10^{-26}$ at 25° C.), zinc ion and oxalic acid (Ksp=$2.5 \times 10^{-9}$ at 25° C.), barium ion and sulfuric ion (Ksp=$1.0 \times 10^{-10}$ at 25° C.), silver ion and hydrochloric acid (Ksp=$1.0 \times 10^{-10}$ at 25° C.) and calcium ion and tartaric acid (solubility at 25° C. is 0.03 g/100 g water).

According to the present invention, the second agent comprises components (B-1) and (B-2). It is necessary that component (B-2) per se never readily permeate into the keratinous fiber in order to secure the action of component (B-2) only on the surface of the keratinous fiber. Furthermore, it is also necessary that the component (B-2) form a complex together with component (A), and the resulting complex be readily soluble in water. By such, component (B-2) and component (B-1) compete with each other for reacting with component (A), which prevents component (B-1) from binding to component (A). Moreover, since the complex of component (B-2) and component (A) per se is readily soluble in water, deposit of water-insoluble salts or sparingly soluble complexes on the surface of the keratinous fiber is reduced. The present invention first achieved imparting sufficient elasticity and firmness to keratinous fibers without causing any objectionable frictional or rough feel to the touch by the addition of the component (B-2).

No limitations are imposed on the component (B-2) of the present invention as long as it is capable of forming a complex together with a metal ion of component (A), and the thus formed complex is readily soluble in water. However, if the molecular weight of component (B-2) is 180 or less, it will easily permeate into the keratinous fibers, and as a result, hinder the deposition of water-insoluble or sparingly soluble complexes due to the bonding of component (A) and component (B) inside the keratinous fibers. This indicates reduced effects of the capability of providing firmness and elasticity to the keratinous fibers. From this point of view, the molecular weight of component (B-2) desirably exceeds 180.

Preferable examples of component (B-2) include polycarbonic acids or oxycarbonic acids such as citric acid, isocitric acid, alloisocitric acid, tricarballylic acid and polyacrylic acid; aminopolycarbonic acids such as nitrilotriacetic acid, nitrilotripropionic acid, ethylenediamine tetraacetic acid and ethylene diamine tetrapropionic acid; and polyphosphonic acids such as aminotrimethylene phosphonic acid, 1-hydroxyethylidene-1,1-diphosphonic acid, ethylenediamine tetramethylenephosphonic acid, hexamethylenediamine tetramethylene phosphonic acid and dimethylenetriamine pentamethylene phosphonic acid.

These components (B-2) may be used singly or in combination of two or more. It is preferred that the component (B-2) be incorporated in the second agent from 0.01 to 20.0%, more preferably from 0.05 to 10.0%. Amounts less than 0.01% cannot successfully reduce the frictional or rough feel to the touch of the fibers due to deposit of the water-insoluble or sparingly soluble complex on the surface of the keratinous fibers. On the other hand, amounts exceeding 20% are not desirable because the formation of water-insoluble or sparingly soluble complexes in keratinous fiber by components (A) and (B) is hindered, as a result, the firmness, elasticity and volume of the keratinous fibers may be reduced.

The first and second agents useful for preparing the present composition can be prepared according to known methods. Both agents of the present composition may contain optional components which are commonly used in the art as long as the effects of the invention are secured. Examples of such optional components include surfactants, thickeners, oils, hair styling bases, pH modifiers, sensation improvers and perfumes.

According to the present invention, the keratinous fibers are treated with the present composition in a following manner. First, the keratinous fibers are treated with the first agent, and after the elapse of a predetermined period of time, the second agent is applied thereto. In more detail, after the keratinous fibers are treated with the first agent, they are allowed to stand for a certain period of time sufficient for allowing metal ion (A) in the first agent to be permeated inside the fiber. It is however preferred that the fibers which had undergone the treatment with the first agent be allowed to stand for 10 to 60 minutes from room temperature to 80° C., followed by intermediate rinsing as required. After the keratinous fibers are treated with the second agent, they are preferably allowed to stand for a certain period of time sufficient for completing the reaction between components (B-1) and (B-2), preferably for 5 to 30 minutes from room temperature to 80° C., subsequently submitted to rinsing with running water and drying.

EXAMPLES

The present invention will now be described in more detail by way of Examples, which however should not be construed as limiting the invention thereto.

Example 1

First agents [1-a] and [1-b] formulated as shown in Table 1 and second agents [2-a] and [2-b] formulated as shown in Table 2 were prepared. A panel consisting of 10 experts compared and organoleptically evaluated the results of treatment according to the present invention and conventional treatment using the prepared agents. The evaluation was made in terms of firmness and elasticity of the hair fiber.

In detail, about 10 g of a blond hair tress of an occidental was treated first with a first agent and subsequently with a second agent. The tested combinations of the first and second agents are shown in Table 3 (left column). First, 5 g of a first agent was applied to the hair, which was allowed to stand for 15 minutes at 45° C., and subsequently, 5 g of a second agent was applied thereto and allowed to stand for 15 minutes at 45° C. The thus treated hair was rinsed with running water, then shampooed and rinsed. For comparison, a similar hair tress as above was treated with either a first agent or a second agent, under exactly the same conditions as described above. The results of comparison concerning the firmness and elasticity of the hair fiber are also shown in Table 3.

The data in Table 3 demonstrate that the treatment of the invention utilizing the invention agents are superior to the comparative examples in firmness and elasticity of the hair fiber.

TABLE 1

Formulation of First Agent

|  | 1-a | 1-b |
|---|---|---|
| Hydroxyethylcellulose | 1.3% | 1.3% |
| Calcium chloride | 1.5% | — |
| Magnesium chloride | — | 1.5% |
| Ion-exchanged water | balance | balance |

TABLE 2

Formulation of Second Agent

|  | 1-a | 1-b |
|---|---|---|
| Hydroxyethylcellulose | 1.3% | 1.0% |
| Oxalic acid | 2.0% | 2.0% |
| 1-Hydroxyethylidene-1,1-disulfonic acid | 1.0% | — |
| Citric acid | — | 1.0% |
| L-arginine | suitable amount | |
| pH | 7.5 | 7.5 |

TABLE 3

| Treatment of Invention | Rank A | Rank B | Rank C | Treatment of Comparison |
|---|---|---|---|---|
| [1-a] → [2-a] | 8 | 2 | 0 | (1-a) |
|  | 10 | 0 | 0 | (2-a) |
| [1-a] → [2-b] | 8 | 2 | 0 | (1-a) |
|  | 9 | 1 | 0 | (2-b) |
| [1-b] → [2-a] | 9 | 1 | 0 | (1-b) |
|  | 10 | 0 | 0 | (2-a) |
| [1-b] → [2-b] | 8 | 2 | 0 | (1-b) |
|  | 9 | 1 | 0 | (2-b) |

Rank A: "Invention treatment is better providing firmness and elasticity".
Rank B: "No difference between Invention and Comparison".
Rank C: "Comparison treatment is better providing firmness and elasticity".

Example 2

A second agent [2-c] formulated as shown in Table 4 was prepared. Combinations of [2-c] and one of the first agents [1-a] and [1-b] which were used in Example 1 were taken as comparison, and the procedures of Example 1 were followed using a hair tress as described in Example 1. A panel consisting of 10 experts compared and evaluated in terms of presence or absence of the rough feel to the touch of the hair. The results are shown in Table 5, too.

The data in Table 5 revealed that the treatments of the present invention which utilize the invention agents secured the same level of firmness and elasticity as comparison, but provided significantly superior results with respect to reduced rough feel.

TABLE 4

Formulation of Second Agent

|  | 2-c |
|---|---|
| Hydroxyethylcellulose | 1.3% |
| Oxalic acid | 2.0% |
| L-arginine | suitable amount |
| pH | 7.5 |

TABLE 5

| Treatment of Invention | Rank A | Rank B | Rank C | Rank D | Rank E | Rank F | Treatment of Comparison |
|---|---|---|---|---|---|---|---|
| [1-a] → [2-a] | 3 | 6 | 1 | 10 | 0 | 0 | [1-a] → [2-c] |
| [1-a] → [2-b] | 2 | 6 | 2 | 8 | 2 | 0 | |
| [1-b] → [2-a] | 3 | 5 | 2 | 9 | 1 | 0 | [1-b] → [2-c] |
| [1-b] → [2-b] | 2 | 7 | 1 | 9 | 1 | 0 | |

Rank A: "Invention treatment is better concerning firmness and elasticity".
Rank B: "No difference between Invention and Comparison".
Rank C: "Comparison treatment is better concerning firmness and elasticity".
Rank D: "Invention treatment provides more reduced rough feel to the touch of the hair than Comparison treatment".
Rank E: "No difference between Invention and Comparison"
Rank F: "Comparison treatment provides more reduced rough feel to the touch of the hair than Invention treatment".

Example 3

Second agents formulated as shown in Table 6 were prepared. Combinations of each of the thus prepared second agents and the first agent [1-a] prepared in Example 1 were respectively applied to 10 g of blond hair tress of an occidental, and beauticians evaluated the firmness and elasticity of the hair fiber.

In detail, about 10 g of the hair tress was first treated with 5 g of the first agent [1-a], allowed to stand for 20 minutes at 45° C., and subsequently treated with 5 g of each of the second agents shown in Table 6, and was allowed to stand for 15 minutes at 45° C. The thus treated hair was rinsed with running water, then shampooed, rinsed and dried. Firmness, elasticity and presence or absence of rough feel to the touch of the hair after treatment were evaluated by beauticians. The results are shown in Table 6.

The data in Table 6 demonstrate that the treatment of the invention utilizing the invention agents are superior to the comparative examples in firmness and elasticity of the hair fiber, providing reduced rough feel to the touch of the hair.
Evaluation standard:
  Firmness and elasticity:
    ⊚: Very firm and elastic
    ○: Fairly firm and elastic Δ: Cannot tell ×: Absence of firmness and elasticity Rough feel to the touch of the treated hair:

⊙: Significantly reduced rough feel

○: Reduced rough feel

Δ: Cannot tell

×: Very rough feel

TABLE 6

|  | Invention | | Comparison | |
|---|---|---|---|---|
|  | [2-d] | [2-e] | [2-f] | [2-g] |
| Hydroxyethylcellulose | 1.3% | 1.3% | 1.3% | 1.3% |
| Tartaric acid | 2.0% | 2.0% | 2.0% | 2.0% |
| Citric acid | 1.5% | — | — | — |
| Ethylenediamine tetraacetic acid | — | 1.5% | — | — |
| Acetic acid | — | — | — | 3.0% |
| L-arginine | ← suitable amount → | | | |
| pH | 7.5 | 7.5 | 7.5 | 7.5 |
| Firmness and elasticity | ⊙ | ⊙ | ⊙ | × |
| Rough feel to the touch | ⊙ | ⊙ | × | ○ |

Industrial Applicability:

When the compositions according to the present invention are used for treating keratinous fibers, they allow water-insoluble or sparingly soluble complexes to deposit inside the keratinous fibers while preventing water-insoluble or sparingly soluble complexes from depositing on the surface of the keratinous fibers. Because of this mechanism, the present compositions are capable of imparting sufficient firmness and elasticity to keratinous fibers without inducing any objectionable rough or frictional feel to the touch of the hair.

We claim:

1. A kit composition for treating keratinous fibers, which comprises a first agent separate from a second agent, said first agent containing an ion of a metal selected from the group consisting of magnesium, calcium, zinc, silver, aluminum, barium, manganese, iron, nickel and mixtures thereof, and wherein said metal ion is contained in said first agent in an amount of from 0.05 to 20.0% by weight, and said second agent comprising:

(B-1) A first organic or inorganic compound or mixtures thereof that is capable of permeating into the keratinous fibers and which forms a water-insoluble or sparingly soluble complex with said metal ion of said first agent, wherein said component (B-1) is contained in said second agent in an amount of from 0.1 to 10.0% by weight based on the total weight of said second agent, and wherein said first organic compound is selected from the group consisting of formic acid, acetic acid, propionic acid, butyric acid, isobutyric acid, valeric acid, isovaleric acid, sorbic acid, lactic acid, oxalic acid, malonic acid, succinic acid, glutaric acid, maleic acid, fumaric acid, citraconic acid, itaconic acid, and salts thereof, and wherein said first inorganic compound is a source of an ion selected from the group consisting of chloride ion, hydroxide ion, nitrite ion, sulfate ion, phosphate ion, borate ion, and carbonate ion, and (B-2) A second organic compound that cannot permeate into the keratinous fibers and which forms a water-soluble complex with said metal ion of said first agent, wherein said component (B-2) is contained in said second agent in an amount of from 0.01 to 20.0% by weight based on the total weight of said second agent, and wherein said second organic compound is selected from the group consisting of a polycarbonic acid, oxycarbonic acid, amino-polycarbonic acid, polyphosphonic acid and mixtures thereof.

2. The composition as defined in claim 1, wherein the solubility in water at 25° C. of the complex formed between said metal ion of said first agent and said component (B-1) is 0.2 g/100 g or less.

3. The composition as defined in claim 1, wherein the metal ion of said first agent is present in the form of a water-soluble salt.

4. A method for treating keratinous fibers which comprises steps A and B:

A: treating keratinous fibers with a first agent containing an ion of a metal selected from the group consisting of magnesium, calcium, zinc, silver, aluminum, barium, manganese, iron, nickel and mixtures thereof; and B: subsequently treating the hair which had undergone step A treatment with a second agent comprising:

a first organic or inorganic compound or mixtures thereof that is capable of permeating into the keratinous fibers and which forms a water-insoluble or sparingly soluble complex with said metal ion of said first agent, wherein said first organic compound is selected from the group consisting of formic acid, acetic acid, propionic acid, butyric acid, isobutyric acid, valeric acid, isovaleric acid, sorbic acid, lactic acid, oxalic acid, malonic acid, succinic acid, glutaric acid, maleic acid, fumaric acid, citraconic acid, itaconic acid, and salts thereof, and wherein said first inorganic compound is a source of an ion selected from the group consisting of chloride ion, hydroxide ion, nitrite ion, sulfate ion, phosphate ion, borate ion, and carbonate ion, and a second organic compound that cannot permeate into the keratinous fibers and which forms a water-soluble complex with said metal ion of said first agent, wherein said second organic compound is selected from the group consisting of a polycarbonic acid, oxycarbonic acid, amino-polycarbonic acid, polyphosphonic acid and mixtures thereof.

5. The method of claim 4, wherein said metal ion is contained in said first agent in an amount of from 0.05 to 20.0% by weight.

6. The method of claim 4, wherein the solubility in water at 25° C. of the complex formed between said metal ion of said first agent and said component (B-1) is 0.2 g/100 g or less.

7. The method of claim 4, wherein said component (B-1) is contained in said second agent in an amount of from 0.1 to 10.0% by weight based on the total weight of said second agent.

8. The method of claim 4, wherein said component (B-2) in contained in said second agent in an amount of from 0.01 to 20.0% by weight based on the total weight of said second agent.

9. The method of claim 4, wherein said first agent is allowed to stand on the treated hair for 10 to 60 minutes at a temperature ranging from room temperature to 80° C. prior to performing step (B).

10. The method of claim 9, wherein said first agent is allowed to stand on the treated hair for 15 minutes at 45° C. prior to performing step (B).

11. The method of claim 4, wherein said second agent is allowed to stand on the treated hair for 5 to 30 minutes at a temperature ranging from room temperature to 80° C.

12. The method of claim 11, wherein said second agent is allowed to stand on the treated hair for 15 minutes at 45° C.

13. The method of claim 4, which further comprises rinsing the treated hair with running water after performing step (B).

* * * * *

UNITED STATES PATENT AND TRADEMARK OFFICE
CERTIFICATE OF CORRECTION

PATENT NO. : 5,472,697
DATED : December 5, 1995
INVENTOR(S) : Yuji HIRANO, et al.

It is certified that error appears in the above-indentified patent and that said Letters Patent is hereby corrected as shown below:

On the title page, Item [87], the PCT Pub. No. should read: --WO94/00099--

Signed and Sealed this

Second Day of April, 1996

Attest:

BRUCE LEHMAN

Attesting Officer

Commissioner of Patents and Trademarks